US008865960B2

(12) United States Patent
Timken et al.

(10) Patent No.: US 8,865,960 B2
(45) Date of Patent: Oct. 21, 2014

(54) STARTUP PROCEDURES FOR IONIC LIQUID CATALYZED HYDROCARBON CONVERSION PROCESSES

(75) Inventors: Hye-Kyung Timken, Albany, CA (US); Howard S. Lacheen, Richmond, CA (US); Shawn S. Winter, Midvale, UT (US)

(73) Assignee: Chevron U.S.A. Inc., San Ramon, CA (US)

( * ) Notice: Subject to any disclaimer, the term of this patent is extended or adjusted under 35 U.S.C. 154(b) by 944 days.

(21) Appl. No.: 12/825,121

(22) Filed: Jun. 28, 2010

(65) Prior Publication Data

US 2011/0319694 A1   Dec. 29, 2011

(51) Int. Cl.
*C07C 2/60* (2006.01)
*C07C 2/62* (2006.01)

(52) U.S. Cl.
CPC ............. *C07C 2/60* (2013.01); *C07C 2531/02* (2013.01); *C07C 2527/125* (2013.01)
USPC ........... 585/719; 585/709; 585/721; 585/722; 585/727; 585/728

(58) Field of Classification Search
CPC ............. C07C 2/00; C07C 2/02; C07C 2/04; C07C 2/06; C07C 2/08; C07C 2/20; C07C 2/22; C07C 2/54; C07C 2/56; C07C 2/58; C07C 2/60; C07C 2/62
USPC .................. 585/719, 709, 721, 722, 727, 728
See application file for complete search history.

(56) References Cited

U.S. PATENT DOCUMENTS

| 4,235,983 | A | 11/1980 | Sroka et al. |
| 4,686,775 | A | 8/1987 | Sandford et al. |
| 7,432,408 | B2 * | 10/2008 | Timken et al. ................. 585/709 |
| 7,495,144 | B2 * | 2/2009 | Elomari ........................ 585/724 |
| 7,531,707 | B2 | 5/2009 | Harris et al. |
| 2003/0199723 | A1 | 10/2003 | Hommeltoft |
| 2006/0020088 | A1 | 1/2006 | Hope et al. |
| 2007/0142686 | A1 | 6/2007 | Campbell et al. |

OTHER PUBLICATIONS

Ying Liu, Ruisheng Hu, Chunming Xu, Haiquan Su, Alkylation of isobutene with 2-butene using composite ionic liquid catalysts, Applied Catalysis A: General, vol. 346, Issues 1-2, Aug. 31, 2008, pp. 189-193, ISSN 0926-860X, 10.1016/j.apcata.2008.05.024.*
Hommeltoft, Sven. Fixed-Bed Alkylation Using SLP-Type Catalyst in a Chromatographic-Type Reactor Concept, Ind. Eng. Chem. Res. 2003, 42, 5526-5534.*
API Recommended Practice 751, Safe Operation of Hydrofluoric Acid Alkylation Units, Third Edition, Jun. 2007.*

* cited by examiner

*Primary Examiner* — In Suk Bullock
*Assistant Examiner* — Philip Louie
(74) *Attorney, Agent, or Firm* — Steven H. Roth; Susan M. Abernathy (57) ABSTRACT

Methods for starting and operating ionic liquid catalyzed hydrocarbon conversion processes and systems to provide maximum process efficiency, system reliability and equipment longevity may include: purging air and free water from at least a portion of the system; introducing at least one reactant into the at least a portion of the system; and re-circulating the at least one reactant through the at least a portion of the system, via at least one feed dryer unit, until the at least one reactant exiting the at least a portion of the system has a water content at or below a threshold value, prior to the introduction of an ionic liquid catalyst and/or additional reactant(s) and feeds into the system.

17 Claims, 5 Drawing Sheets

STARTUP PROCEDURES FOR IONIC LIQUID CATALYZED HYDROCARBON CONVERSION PROCESSES

FIELD OF THE INVENTION

The present invention relates to startup procedures for ionic liquid catalyzed hydrocarbon conversion processes.

BACKGROUND OF THE INVENTION

Metal halide ionic liquid catalysts are attractive in many refinery process applications where the liquid catalyst is easily mixed with the reactants in a reactor, and readily separated from hydrocarbon products in a settler. Ionic liquid catalysts may be used in a range of hydrocarbon conversion processes, such as paraffin alkylation, paraffin isomerization, olefin isomerization, olefin dimerization, olefin oligomerization, olefin polymerization and aromatic alkylation.

An example of an ionic liquid catalyzed hydrocarbon conversion process is the alkylation of isoparaffins with olefins to make gasoline cuts with high octane number (see, e.g., U.S. Pat. No. 7,432,408 to Timken et al.). In contrast, a widely used conventional process for the alkylation of isoparaffins with olefins is catalyzed by sulfuric acid or hydrofluoric acid. Apart from environmental, health and safety concerns related to the use of large volumes of $H_2SO_4$ or HF, ionic liquid catalyzed alkylation offers a number of advantages over conventional alkylation, including: lower capital expenditure on plants, lower operating expenditure, lower catalyst inventory volume, lower catalyst make-up rate, expansion of usable feeds, and higher gasoline yield.

The presence of HCl as a co-catalyst with an ionic liquid provides an increased level of catalytic activity, for example, as disclosed by U.S. Pat. No. 7,432,408. Typically, anhydrous HCl or organic chloride is added with the reactor feed to direct the reactions to the desired activity and selectivity (see, e.g., U.S. Pat. No. 7,495,144 to Elomari, and U.S. Pat. No. 7,531,707 to Harris et al.). In the case of organic chloride as co-catalyst, HCl may be formed in situ in the reactor. However, the presence of HCl in the downstream product separation sections of the plant may corrode distillation columns and other equipment, especially if there is any water present. Accordingly it is important to avoid the introduction of water during ionic liquid catalyzed hydrocarbon conversion processes.

There is a need for a systematic startup procedure for ionic liquid catalyzed hydrocarbon conversion processes, including alkylation processes for alkylate gasoline manufacture, not only to optimize the process performance and efficiency, but also to increase plant reliability and prolong the useful life of the equipment.

SUMMARY OF THE INVENTION

The present invention provides startup procedures for greatly improving the performance of ionic liquid catalyzed hydrocarbon conversion processes. In an embodiment, a startup procedure of the present invention also substantially decreases equipment maintenance and extends the life of the equipment used in systems for performing such ionic liquid catalyzed hydrocarbon conversion processes.

According to one aspect of the present invention there is provided a method for operating an ionic liquid catalyzed hydrocarbon conversion system, the method comprising purging air and free water from at least a portion of the system; introducing at least one reactant into the at least a portion of the system; via at least one feed dryer unit, re-circulating the at least one reactant through the at least a portion of the system until the at least one reactant exiting the at least a portion of the system has a water content at or below a threshold value; and after the re-circulating step, introducing an ionic liquid catalyst into a reactor of the system.

In an embodiment, the present invention also provides a method for operating an ionic liquid catalyzed hydrocarbon conversion system, the method comprising purging air and free water from the system, wherein the system comprises a reactor, a distillation unit in fluid communication with the reactor, and a catalyst regeneration unit in fluid communication with the reactor; introducing at least one reactant into the system; via at least one feed dryer unit, re-circulating the at least one reactant through the system until the at least one reactant exiting the system has a water content at or below a threshold value; after the water content has attained the threshold value, introducing a catalyst promoter into the reactor; and after introducing the catalyst promoter, introducing an ionic liquid catalyst into the reactor.

In another embodiment, the present invention provides a method for operating an ionic liquid catalyzed hydrocarbon conversion system, the method comprising purging air and free water from the system, wherein the system comprises a reactor, a distillation unit in fluid communication with the reactor, and a catalyst regeneration unit in fluid communication with the reactor; recycling a dried feed through the system, via a feed dryer unit, until the residual water content of the feed is at or below a threshold value; after the water content has attained the threshold value, introducing at least one reactant into the reactor; and after initiation of the step for introducing reactant(s), introducing a catalyst promoter into the reactor. After initiation of the step for introducing the catalyst promoter, the method further comprises: introducing an ionic liquid catalyst into the reactor; contacting the at least one reactant with the ionic liquid catalyst in the reactor to form at least one hydrocarbon product; separating the ionic liquid catalyst from a hydrocarbon phase containing the at least one hydrocarbon product; feeding at least a portion of the hydrocarbon phase to the distillation unit; adjusting the distillation conditions of the distillation unit to provide the at least one hydrocarbon product under steady state distillation conditions; and adjusting the catalyst regeneration unit to provide steady state catalytic activity of the reactor.

DETAILED DESCRIPTION

Ionic liquid catalysts are useful for a range of hydrocarbon conversion processes, including paraffin alkylation, paraffin isomerization, olefin isomerization, olefin dimerization, olefin oligomerization, olefin polymerization and aromatic alkylation. Applicants have now discovered that the use of an appropriate startup procedure can greatly improve the performance of ionic liquid catalyzed hydrocarbon conversion processes and can also extend the life of the equipment used in performing such processes.

Startup Procedure for Ionic Liquid Catalyzed Hydrocarbon Conversions

According to one aspect of the present invention, a startup procedure for an ionic liquid catalyzed hydrocarbon conversion system may be performed as follows:
1) Purge of the system with dry inert gas;
2) Activation of dryerants for feeds; and
3) Purge of the system with dry feed(s) to a threshold level of residual water.

In an embodiment, item 1) may comprise purging the system with dry nitrogen gas to remove any trapped air and free water. In another embodiment, item 1) may comprise purging the system with a dry hydrocarbon gas. In an embodiment where, as an example only, the purge gas in item 1) is a dry isoparaffin, and the feed in item 3) is the same isoparaffin, items 1) and 3) may be combined into a single step. In another embodiment, item 3) may be performed after item 1), e.g., the system may be purged first with dry nitrogen gas in item 1), and thereafter the system may be purged with dry isobutane in item 3). In an embodiment, item 2) may comprise passing dry nitrogen gas through a dryerant, such as a molecular sieve, at an elevated temperature for an extended period of time (e.g., up to several hours). In an embodiment, the threshold residual water content according to item 3) may generally be less than about 10 ppm.

After the purge with dry feeds to the threshold level of residual water, the following may be performed:
4) Introduction of reactant(s) into the system;
5) Introduction of a catalyst promoter or co-catalyst;
6) Introduction of ionic liquid catalyst;
7) Line-out of the distillation section to provide steady state product purification;
8) Generation of product(s); and
9) Line-out of the catalyst regeneration unit and/or catalyst draining to maintain steady state catalytic activity and hydrocarbon conversion process performance.

In an embodiment, the reactant(s) introduced according to item 4) may comprise an isoparaffin, e.g., a $C_4$-$C_6$ isoparaffin, or an olefin, such as a $C_2$-$C_6$ olefin, or both an isoparaffin and an olefin. In an embodiment, the catalyst promoter may comprise HCl or organic halide. Such a promoter may also be referred to herein as a co-catalyst.

According to one aspect of the present invention, a procedure as described hereinabove may be applied, for example, to an ionic liquid catalyzed hydrocarbon conversion system that is undergoing an initial startup, or to a system that has been taken out of service for a period of time and entirely emptied and cleaned. According to another aspect of the present invention, a system that was previously operated and subsequently shut down for service or maintenance of only a portion of the system, may undergo a simpler startup procedure. For example, depending on the particular portion(s) of the system involved in a service operation, some of the steps described herein, e.g., with reference to Example 2, may be omitted.

Startup Procedure for Ionic Liquid Catalyzed Alkylation

According to an embodiment of the present invention, a startup process for an ionic liquid catalyzed hydrocarbon alkylation process may include the following:
i. Purge of an ionic liquid catalyzed alkylation system with inert gas to remove any trapped air and free water;
ii. Activation of dryerants for feeds; and
iii. Purge of the system with dry feed(s) to a threshold level of residual water.

In an embodiment, items i. and iii. may be performed substantially as described hereinabove for items 1)-3). The threshold level of residual water of item iii) may generally be less than about 10 ppm.

After the purge with dry feed(s) to the threshold level of residual water, the following may be performed:
iv. Introduction of isoparaffin reactant to the system;
v. Introduction of HCl or organic halide catalyst promoter;
vi. Introduction of ionic liquid catalyst;
vii. Introduction of olefin feed;
viii. Line-out of the distillation section to provide steady state purification of alkylate product;
ix. Generation of alkylate product; and
x. Line-out of the regeneration section and/or catalyst draining to maintain steady state catalytic activity and alkylation process performance.

In an embodiment, items iv. through x. may be performed in the order given. In other embodiments, items iv. through x. may be performed in a different order or concurrently.

Hydrocarbon Conversion Systems

Figure 1:
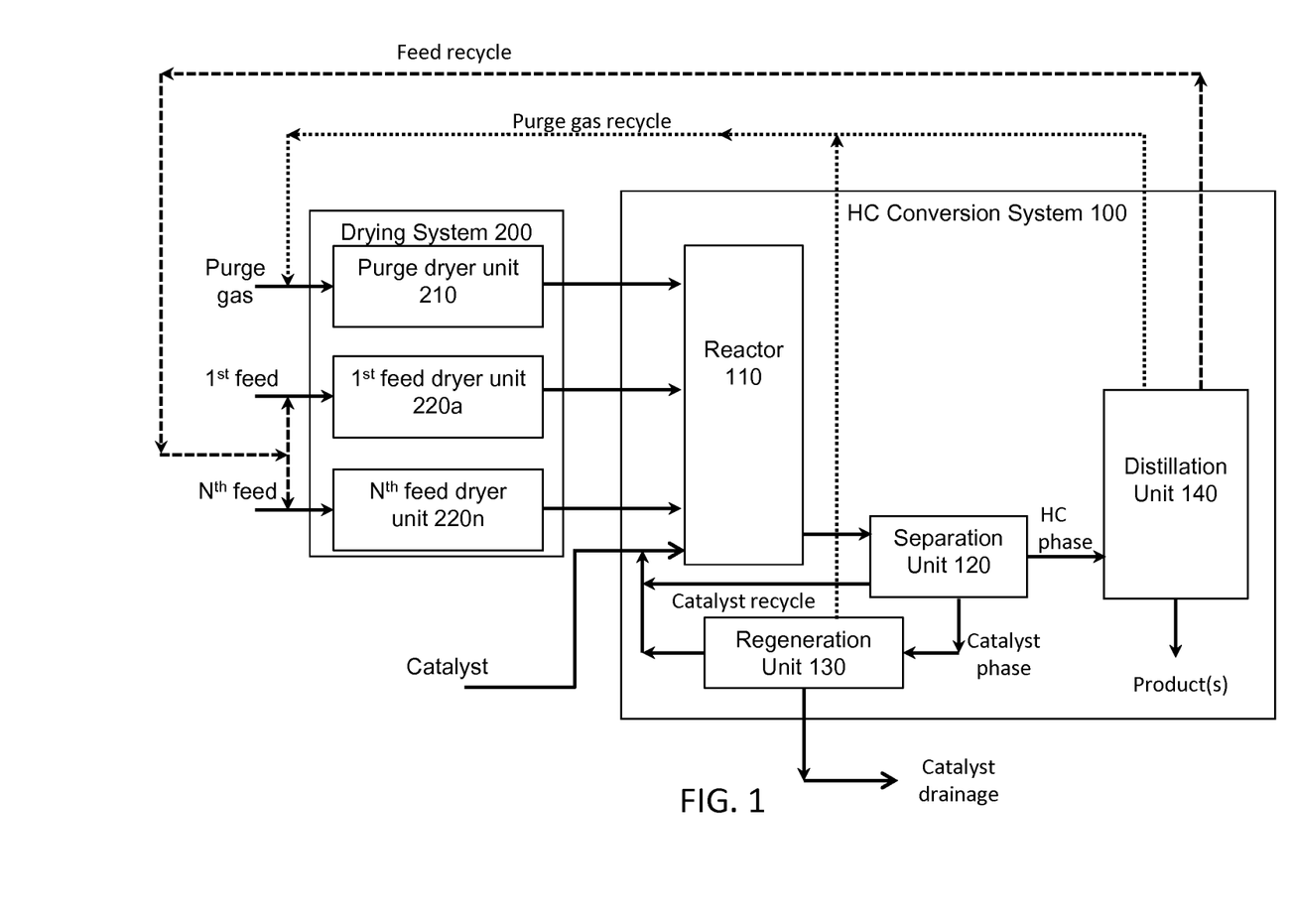
FIG. 1 is a block diagram representing a scheme for an ionic liquid catalyzed hydrocarbon conversion process, according to an embodiment of the invention.

With reference to FIG. 1, an ionic liquid catalyzed hydrocarbon conversion system 100 according to an embodiment of the present invention may include a reactor 110, a separation unit 120, a regeneration unit 130, and a distillation unit 140. Reactor 110 may be in fluid communication with separation unit 120. Separation unit 120 may be in fluid communication with catalyst regeneration unit 130 and with distillation unit 140. Catalyst regeneration unit 130 may be in fluid communication with reactor 110 for feeding regenerated catalyst to reactor 110.

Ionic liquid catalyzed hydrocarbon conversion system 100 may be in fluid communication with a drying system 200. In an embodiment, drying system 200 may include a plurality of feed dryer units, represented in FIG. 1 by a first feed dryer unit 220a and an $N^{th}$ feed dryer unit 220n. The number of feed dryer units may vary, e.g., according to the number of feeds to conversion system 100. The number of feeds to conversion system 100 may in turn depend on a particular hydrocarbon conversion process to be performed using conversion system 100. In an embodiment, the number of feeds to conversion system 100 may be generally in the range from about one (1) to four (4), and typically from about two (2) to three (3). In an embodiment, the feeds for conversion system 100 may include at least one reactant and at least one catalyst.

In an embodiment, each dryer unit may be used to effectively dry a fluid to a water content of not more than about 10 ppm, in a sub-embodiment not more than about 5 ppm, and in another sub-embodiment not more than about 1 ppm. The fluid to be dried by the dryer units of drying system 200 may comprise a gas, e.g., purge gas, or a liquid, e.g., a co-catalyst or reactant feed. As non-limiting examples, the purge gas may comprise dry nitrogen or dry isobutane.

According to an aspect of the present invention, dry purge gas may be passed through conversion system 100 to remove air and free water from all or at least a portion thereof. In an embodiment, dry purge gas may be passed once through conversion system 100. In another embodiment as shown in FIG. 1, drying system 200 may include a purge dryer unit 210, and the purge gas may be recycled through conversion system 100 via purge dryer unit 210. As an example only, purge dryer unit 210 may be used to effectively dry purge gas to a water content of about 10 ppm or less. According to an embodiment of the invention involving a complete or initial startup of conversion system 100, the entire system 100 may be purged with purge gas. In another embodiment, e.g., involving a procedure to re-start a previously operated conversion system 100, only a portion of system 100 may be purged with the dry purge gas. The portion(s) of conversion system 100 involved in the re-start procedure may include reactor 110, separation unit 120, regeneration unit 130, distillation unit 140, or any combination thereof.

In an embodiment, feed dryer units 220a-220n may be used to effectively dry one or more feeds to a water content of not more than about 10 ppm, not more than about 5 ppm, or not more than about 1 ppm. Each of feed dryer units 220a-220n may comprise one or more vessels. The feeds to system 100 may include reactant(s) and catalyst promoter. Each feed may be dried using a dedicated dryer unit. For example, a first reactant, a second reactant, and a catalyst promoter may be dried using a first, a second, and a third feed dryer unit, respectively. Each vessel of the plurality of dryer units may contain a dryerant, such as a molecular sieve or other adsorbent. The dryerant in each vessel may be activated using dry nitrogen gas flow through the vessel at an elevated temperature.

Figure 2:
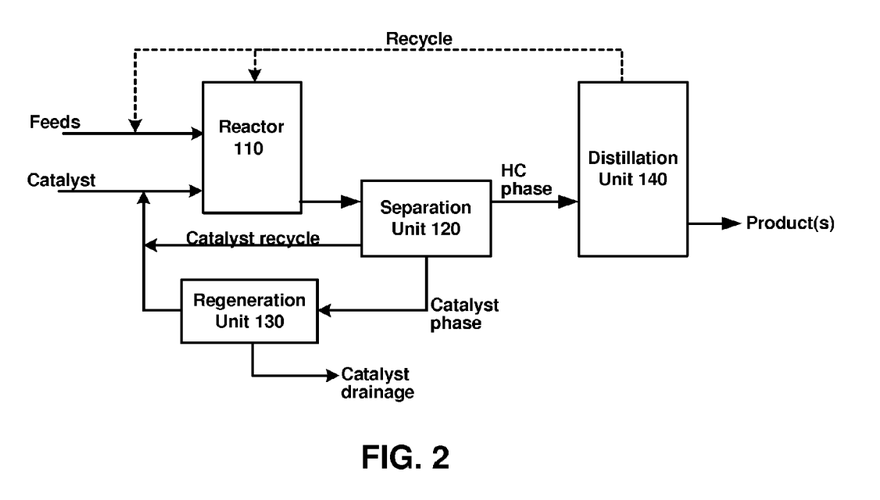
FIG. 2 is a block diagram representing a scheme for an ionic liquid catalyzed hydrocarbon conversion process, according to an embodiment of the invention.

FIG. 2 is a block diagram representing a scheme for an ionic liquid catalyzed hydrocarbon conversion process, according to an embodiment of the present invention. During an ionic liquid catalyzed hydrocarbon conversion process, dry feeds may be introduced into reactor 110, e.g., substantially as described with reference to FIG. 1, supra. The dry feeds may include one or more reactants, which may be introduced into reactor 110 via one or more reactor inlet ports (not shown). Ionic liquid catalyst may be introduced into reactor 110 via a separate inlet port. Reactor 110 may be vigorously stirred to promote contact between reactant(s) and ionic liquid catalyst. Reactor conditions may be adjusted to optimize process performance for a particular hydrocarbon conversion process of the invention.

During hydrocarbon conversion processes of the invention, reactor 110 may contain a mixture comprising ionic liquid catalyst and a hydrocarbon phase. The hydrocarbon phase may comprise one or more hydrocarbon products. The ionic liquid catalyst may be separated from the hydrocarbon phase via separation unit 120, e.g., comprising a settler; and the hydrocarbon and ionic liquid catalyst phases may be allowed to settle under gravity. The bulk of the heavier ionic liquid catalyst phase may be recycled to reactor 110.

With continued operation of conversion system 100, the ionic liquid catalyst may tend to become partially inactivated or spent. Catalyst inactivation is associated with the formation of conjunct polymer in the ionic liquid phase, for example, as disclosed in commonly assigned U.S. Pat. No. 7,674,739, the disclosure of which is incorporated by reference herein in its entirety. In order to maintain the catalytic activity, a portion of the ionic liquid catalyst phase may be fed to regeneration unit 130 for catalyst regeneration. Thereafter, the regenerated ionic liquid catalyst may be recycled to reactor 110. As an example, a process for the regeneration of ionic liquid catalyst is disclosed in U.S. Pat. No. 7,674,739, incorporated by reference herein.

The hydrocarbon phase from separation unit 120 may be fed to distillation unit 140. Distillation unit 140 may represent or comprise a plurality of distillation columns. In an embodiment, distillation unit 140 may comprise one (1), two (2), three (3), four (4), or more distillation columns.

According to one aspect of the instant invention, distillation unit 140 may be adjusted, e.g., with respect to temperature and pressure, to provide one or more hydrocarbon products from the hydrocarbon phase under steady state distillation conditions.

Distillation unit 140 may also separate unreacted feed(s) and/or by-products from reactor 110. For example, one or more reactants may be separated via distillation unit 140 and recycled to reactor 110. In an embodiment, hydrogen chloride may also be separated via distillation unit 140 and recycled to reactor 110. The hydrocarbon products from distillation unit 140 may be further treated, as appropriate, to remove any trace impurities from the final product(s). As a non-limiting example, a hydrocarbon conversion process of the instant invention may comprise an alkylation process, and a product obtained from the distillation unit may comprise an alkylate gasoline or alkylate distillate, as described hereinbelow.

Figure 3:
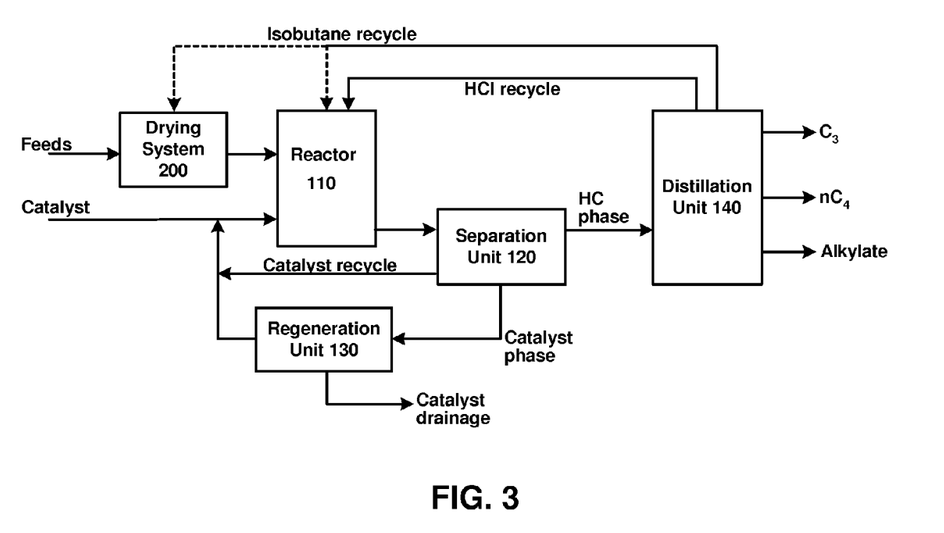
FIG. 3 is a block diagram representing a scheme for an ionic liquid catalyzed alkylation process, according to an embodiment of the invention.

FIG. 3 is a block diagram representing a scheme for an ionic liquid catalyzed alkylation process, according to another embodiment of the invention. An alkylation process according to the scheme of FIG. 3 may be performed using a hydrocarbon conversion system comprising a reactor 110, a separation unit 120, a regeneration unit 130, and a distillation unit 140, substantially as described with reference to FIG. 1. Dry feeds may be introduced into reactor 110 via a drying system 200. Drying system 200 may comprise a plurality of feed dryer units 220a-220n, substantially as described with reference to FIG. 1. The feeds may include a catalyst promoter, such as anhydrous HCl or an alkyl halide. In an embodiment, the catalyst promoter may comprise a $C_2$-$C_6$ alkyl chloride. In a sub-embodiment, the catalyst promoter may comprise n-butyl chloride or t-butyl chloride.

In an embodiment, the alkylation process may involve an isoparaffin-olefin alkylation reaction. In an embodiment, the reactants may include a $C_4$-$C_{10}$ isoparaffin and a $C_2$-$C_{10}$ olefin. In a sub-embodiment, the isoparaffin reactant may comprise isobutane, as exemplified in FIG. 3. It is to be understood that the scheme of FIG. 3 is not limited to an isobutane feed.

With further reference to FIG. 3, fresh ionic liquid catalyst may be introduced into reactor 110, substantially as described with reference to FIG. 2. The catalytic activity of reactor 110 may be maintained under steady state conditions by monitoring the catalytic activity, and by adjusting process parameters, such as the degree of catalyst regeneration, the amount of catalyst drainage, the amount of fresh ionic liquid introduced, and combinations thereof, according to the monitored catalytic activity. The catalytic activity may be gauged by monitoring the conjunct polymer concentration in the ionic liquid catalyst phase. In an embodiment, the catalytic activity may be monitored by analysis of the alkylate product, e.g., for the presence of unreacted olefin(s), the boiling point distribution, and the octane number (see, e.g., U.S. Pat. No. 7,432,408, incorporated by reference herein).

The hydrocarbon phase from separation unit 120 may be fed to distillation unit 140, e.g., substantially as described with reference to FIG. 2. In an embodiment, the alkylate product may comprise $C_{5+}$ alkylate, and in a sub-embodiment predominantly $C_5$-$C_{16}$ alkylate. As a non-limiting example, using isobutane as the isoparaffin feed in an isoparaffin-olefin alkylation reaction, cuts from distillation unit 140 may include HCl, isobutane, propane, n-butane, and alkylate product.

The HCl from distillation unit 140 may be recycled to reactor 110, thereby decreasing the make-up rate for HCl or organic chloride promoter. The unreacted isobutane may also be recycled from distillation unit 140 to reactor 110, thereby further increasing process efficiency. Moreover, the anhydrous operation of the conversion system, including distillation unit 140, allows the isobutane stream to be recycled directly to the reactor 110, i.e., without further drying. Furthermore, the anhydrous operation of conversion system 100 may also allow components of distillation unit 140 to be constructed using relatively low cost materials, such as carbon steel.

System Preparation for Ionic Liquid Catalyzed Hydrocarbon Conversions

Figure 4A:
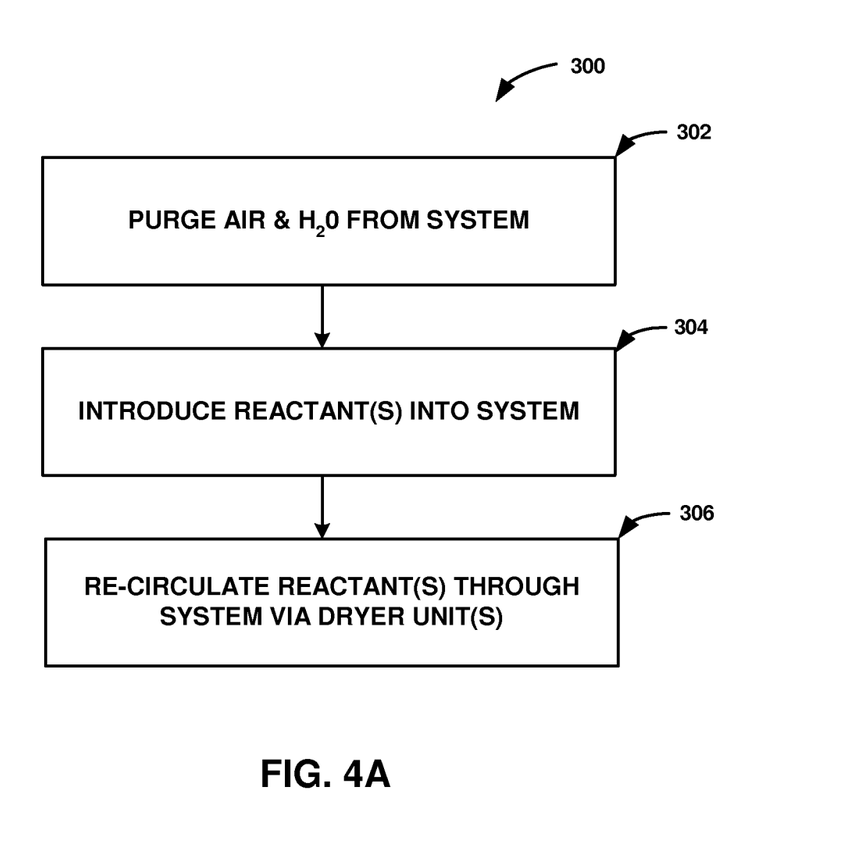
FIG. 4A schematically represents steps involved in a method for preparing a system for an ionic liquid catalyzed hydrocarbon conversion process, according to an embodiment of the invention.

FIG. 4A schematically represents steps involved in a method 300 for preparing a system for an ionic liquid catalyzed hydrocarbon conversion process, according to an embodiment of the invention. Step 302 of method 300 may involve purging any air and/or free water from at least a portion of an ionic liquid catalyzed hydrocarbon conversion system. The hydrocarbon conversion system may include a reactor, a separation unit, a distillation unit, and a catalyst regeneration unit (see, e.g., FIG. 1). The at least a portion of the system may be selected from the reactor, the separation unit, the distillation unit, and the catalyst regeneration unit, or any combination thereof including all of the system components; i.e., in an embodiment, step 302 may involve removing air and/or free water from the entire hydrocarbon conversion system. The hydrocarbon conversion system, or a portion thereof, may be purged by passing dry purge gas through. In an embodiment, the purge gas may comprise dry nitrogen gas. In another embodiment, the purge gas may comprise a light hydrocarbon gas, e.g., dry isobutane.

Step 304 may involve introducing at least one reactant into the hydrocarbon conversion system or a portion thereof. In an embodiment the at least one reactant may comprise a first reactant and a second reactant. In an embodiment, the at least one reactant may comprise a $C_4$-$C_{10}$ isoparaffin and/or a $C_2$-$C_{10}$ olefin. The at least one reactant may be thoroughly dried prior to its introduction into the system. As a non-limiting example, the at least one reactant may be thoroughly dried to a water content of about 10 ppm or less by a feed dryer unit. The feed dryer unit may comprise a vessel containing a suitable dryerant or adsorbent. In an embodiment, the dryerant may comprise a molecular sieve. In a sub-embodiment, the dryerant may comprise 13X or 5A, or 4A or 3A molecular sieve.

The dryerant or molecular sieve may be activated prior to use, e.g., by passing dry nitrogen gas through the dryerant or molecular sieve at an elevated temperature. As a non-limiting example, the dryerant or molecular sieve may be activated by passing dry nitrogen gas through the dryerant or molecular sieve at a temperature generally in the range from about 300 to 750° F., more typically from about 350 to 700° F., and often from about 400 to 600° F. for a time period generally in the range from about 2 to 48 hours, and typically from about 12 to 36 hours.

Step 306 may involve re-circulating the at least one reactant through the system or a portion thereof via at least one feed dryer unit, whereby water is removed from the at least one reactant; and returning the at least one reactant from the at least one feed dryer unit to the at least a portion of the system. In an embodiment, the at least one reactant may be re-circulated through the at least a portion of the system until the at least one reactant exiting the at least a portion of the system has a water content at or below a threshold value. In an embodiment, the threshold value may be not more than about 10 ppm. In a sub-embodiment, the threshold value may be not more than about 5 ppm, and in a further sub-embodiment not more than about 1 ppm. The moisture content of the circulating reactant may be monitored via one or more on-line moisture analyzers. In a sub-embodiment, the at least one reactant may comprise isobutane.

After the at least one reactant exiting the system has attained a water content at or below the threshold value, the system is ready for the introduction of one or more of a catalyst promoter, an ionic liquid catalyst, and additional reactant(s) into the hydrocarbon conversion system (see, e.g., FIG. 4B, infra). According to an aspect of the present invention, various additional steps, e.g., selected from steps 408 through 412 of method 400, may be performed in conjunction with steps 302 through 306.

Operation of Ionic Liquid Catalyzed Hydrocarbon Conversion Systems

Figure 4B:
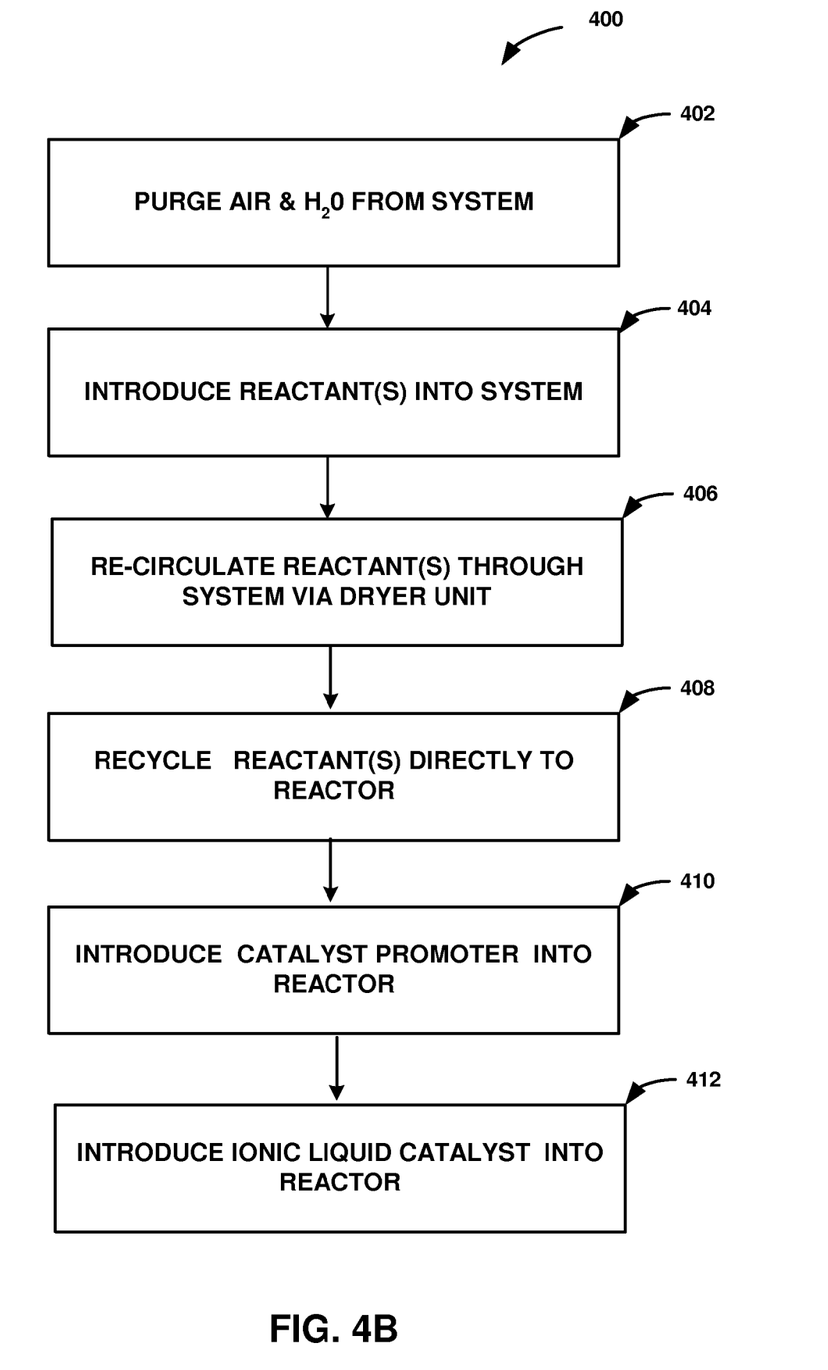
FIG. 4B schematically represents steps involved in a method for operating an ionic liquid catalyzed hydrocarbon conversion system, according to an embodiment of the invention.

FIG. 4B schematically represents steps involved in a method for operating an ionic liquid catalyzed hydrocarbon conversion system, according to another embodiment of the invention. The system may be used for a range of ionic liquid catalyzed hydrocarbon conversion processes. As non-limiting examples, such ionic liquid catalyzed hydrocarbon conversion processes may include: paraffin alkylation, paraffin isomerization, olefin isomerization, olefin dimerization, olefin oligomerization, olefin polymerization, and aromatic alkylation.

The hydrocarbon conversion system may include a reactor and a distillation unit (see, e.g., FIG. 1). The hydrocarbon conversion system may be in fluid communication with a drying system for receiving dry feeds from the drying system and for re-circulating cuts from the distillation unit to the drying system (see, e.g., FIG. 1). The distillation unit may be in fluid communication with the reactor for recycling unreacted feed(s) or other distillation cuts (e.g., anhydrous HCl) to the reactor. In an embodiment, the system may further include a separation unit in fluid communication with the reactor and with a catalyst regeneration unit.

Steps 402 through 406 of method 400 may be performed substantially as described with reference to FIG. 4A. After the threshold value for reactant water content has been attained according to step 406, step 408 may involve recycling the at least one reactant directly to the reactor. For example, step 408 may involve feeding the at least one reactant to the reactor from a downstream portion of the system, without further drying of the at least one reactant stream. As non-limiting examples, the at least one reactant recycled in step 408 may comprise an isoparaffin or an olefin. In an embodiment, the at least one reactant may comprise a $C_4$-$C_{10}$ isoparaffin or a $C_2$-$C_{10}$ olefin. In a sub-embodiment, the at least one reactant may comprise isobutane.

Step 410 may involve introducing a catalyst promoter into the hydrocarbon conversion system. In an embodiment, step 410 may be performed after the initiation of step 404 and prior to the initiation of step 412. The catalyst promoter may comprise anhydrous HCl or an alkyl halide.

Step 412 may involve introducing an ionic liquid catalyst into the reactor. The ionic liquid catalyst may comprise a chloroaluminate ionic liquid, e.g., selected from the group consisting of 1-butyl-4-methyl-pyridinium heptachlorodialuminate, N-butylpyridinium heptachlorodialuminate, 1-butyl-3-methyl-imidazolium heptachlorodialuminate and 1-H-pyridinium heptachlorodialuminate. The activity of the ionic liquid catalyst in the reactor may be monitored and adjusted for steady state catalytic activity, substantially as described hereinabove.

Figure 5:
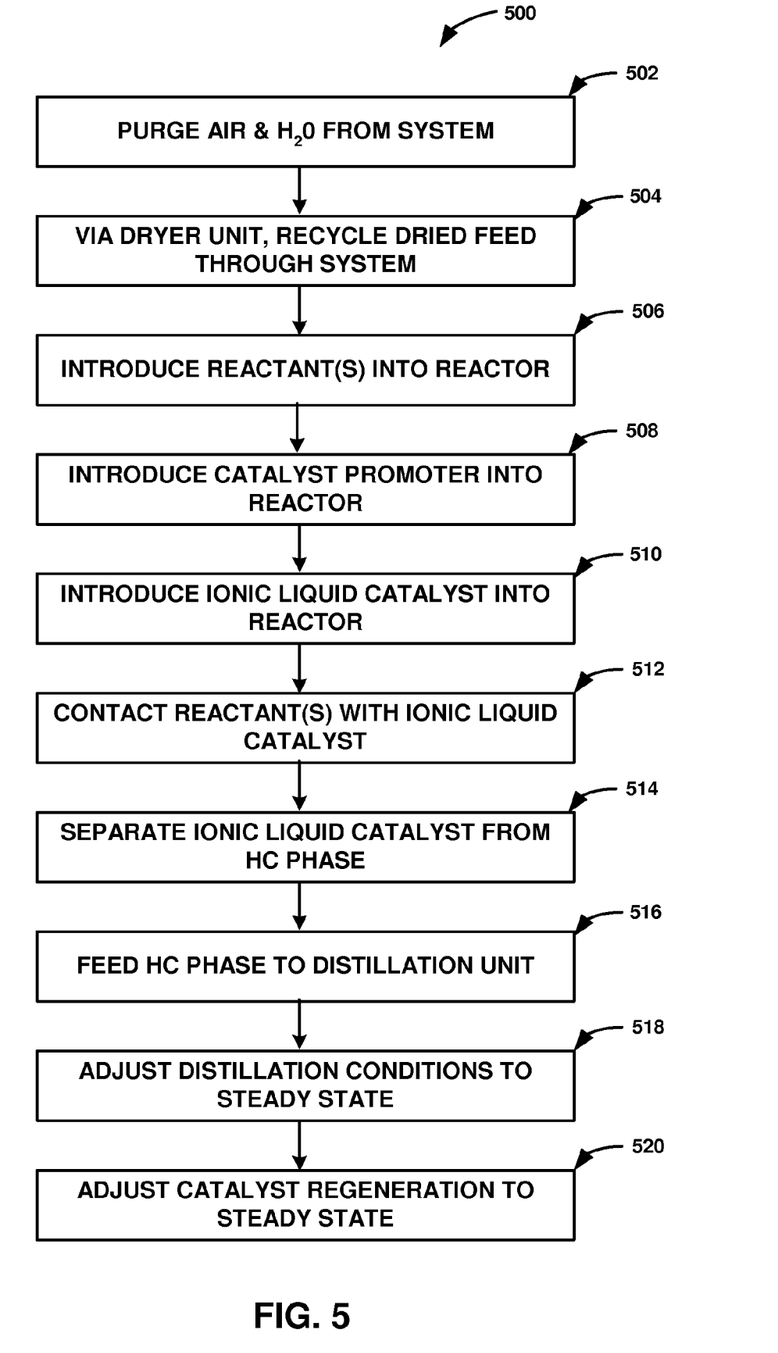
FIG. 5 schematically represents steps involved in a method for operating an ionic liquid catalyzed hydrocarbon conversion system, according to another embodiment of the invention.

After step 412, various additional steps, e.g., selected from steps 512 through 520 of method 500, may be performed in conjunction with steps 402 through 412 to provide at least one hydrocarbon product under efficient, steady state operating conditions.

FIG. 5 schematically represents steps involved in a method for operating an ionic liquid catalyzed hydrocarbon conversion system, according to another embodiment of the invention. Step 502 of method 500 may involve purging air and free water from the system. The system may comprise a reactor, a distillation unit in fluid communication with the reactor, and a catalyst regeneration unit in fluid communication with the reactor. Step 504 may involve recycling a dry feed through the system, via a feed dryer unit, until the residual water content of the feed is at or below a threshold value. In an embodiment, the threshold value may generally be not more than about 10 ppm, and typically not more than about 5 ppm. In an embodiment, the dry feed may comprise a $C_4$-$C_{10}$ isoparaffin.

After the water content has attained the threshold value according to step 504, step 506 may involve introducing at least one reactant into the reactor. In an embodiment, the reactant(s) may comprise an isoparaffin or an olefin. In an embodiment, the reactant(s) of step 506 may comprise the dry feed of step 504, such that step 506 may be a continuation of, or combined with, step 504. In an embodiment, the method may include an alkylation process, wherein step 506 may comprise introducing an isoparaffin, and thereafter step 506 may further comprise introducing an olefin into the reactor. In an embodiment, the isoparaffin may be introduced before step 508, and the olefin may be introduced after steps 508 and 510 (see, e.g., Example 2).

Step 508 may involve introducing a catalyst promoter into the reactor, wherein step 508 may be preformed after the initiation of step 506. In an embodiment, the catalyst promoter may comprise anhydrous HCl or an alkyl halide. Step 510 may involve introducing an ionic liquid catalyst into the reactor. In an embodiment, step 510 may be performed after initiation of step 508. The ionic liquid catalyst may comprise a chloroaluminate, such as N-butylpyridinium heptachlorodialuminate.

Step 512 may involve contacting the at least one reactant with the ionic liquid catalyst in the reactor to form at least one hydrocarbon product. Step 514 may involve separating the ionic liquid catalyst from a hydrocarbon phase containing the at least one hydrocarbon product. The more dense ionic liquid catalyst may be separated from the hydrocarbon phase in a separator. Thereafter, at least a portion of the ionic liquid catalyst may be returned to the reactor for participating in further hydrocarbon conversion reactions.

The ionic liquid catalyst may be subject to deactivation with continued use. Accordingly, a variable portion of the ionic liquid catalyst may be fed to the catalyst regeneration unit, and the regenerated catalyst may then be returned to the reactor. In this way the catalytic activity of the ionic liquid catalyst may be maintained at about a constant level. The catalytic activity and the volume of ionic liquid catalyst may also be maintained at about a constant level by draining portions of partially spent catalyst and/or by adding fresh catalyst to the reactor. By adjusting both the catalytic activity and the volume of the ionic liquid catalyst, the reactor section of the hydrocarbon conversion system can be stabilized, thus allowing the ionic liquid catalyzed hydrocarbon conversion processes of the invention to operate under steady state conditions.

Step 516 may involve feeding at least a portion of the hydrocarbon phase to the distillation unit. The hydrocarbon phase may comprise at least one hydrocarbon product. In an embodiment, the hydrocarbon product may comprise an alkylate product obtained by reaction of an isoparaffin with an olefin. In a sub-embodiment, the at least one hydrocarbon product may comprise a $C_{5+}$ alkylate. Step 518 may involve adjusting distillation conditions of the distillation unit to provide the at least one hydrocarbon product under steady state distillation conditions.

Step 520 may involve adjusting the catalyst regeneration unit to provide steady state catalytic activity of the reactor. In an embodiment, step 520 may involve adjusting the severity of catalyst regeneration and/or adjusting the amount of any catalyst draining from the system. By operating the entire system under steady state conditions, the efficiency of the hydrocarbon conversion processes of the invention may be maximized, while shutdown and maintenance of the system can be minimized.

Feedstocks

In an embodiment, feeds for the present invention may comprise various streams in a petroleum refinery, a gas-to-liquid conversion plant, a coal-to-liquid conversion plant, or in naphtha crackers or wax crackers, e.g., streams containing isoparaffins or olefins. Examples of olefin containing streams include FCC offgas, coker gas, olefin metathesis unit offgas, polyolefin gasoline unit offgas, methanol to olefin unit offgas, FCC light naphtha, coker light naphtha, Fisher-Tropsch unit condensate, and cracked naphtha. Some olefin containing streams may contain two or more olefins selected from ethylene, propylene, butylenes, pentenes, and up to $C_{10}$ olefins. Such streams may be fed to the reactor of a hydrocarbon conversion system of the invention via one or more feed dryer units. Examples of isoparaffin containing streams include, but are not limited to, FCC naphtha, hydrocracker naphtha, coker naphtha, Fisher-Tropsch unit condensate, and cracked naphtha. Such streams may comprise a mixture of two or more isoparaffins. Isobutane may be obtained, for example, from a hydrocracking unit or may be purchased.

Ionic Liquid Catalysts

In an embodiment, processes according to the present invention may use a catalytic composition comprising at least one aluminum halide and at least one quaternary ammonium halide and/or at least one amine halohydride. The ionic liquid catalyst can by any halogen aluminate ionic liquid catalyst comprising an alkyl substituted pyridinium halide or an alkyl substituted imidazolium halide of the general formulas A and B, respectively.

A

B where R═H, methyl, ethyl, propyl, butyl, pentyl or hexyl group and X is a halide and preferably a chloride, and $R_1$ and $R_2$═H, methyl, ethyl, propyl, butyl, pentyl or hexyl group and where $R_1$ and $R_2$ may or may not be the same.

An exemplary aluminum halide that may be used in accordance with the present invention is aluminum chloride ($AlCl_3$). Quaternary ammonium halides which can be used in accordance with the present invention include those described in U.S. Pat. No. 5,750,455, the disclosure of which is incorporated by reference herein.

In an embodiment, the ionic liquid catalyst may be a chloroaluminate ionic liquid prepared by mixing $AlCl_3$ and a hydrocarbyl substituted pyridinium halide, a hydrocarbyl substituted imidazolium halide, a trialkylammonium hydrohalide, or a tetraalkylammonium halide, as disclosed in commonly assigned U.S. Pat. No. 7,495,144, the disclosure of which is incorporated by reference herein in its entirety.

Reaction Conditions

Due to the low solubility of hydrocarbons in ionic liquids, hydrocarbon conversion reactions in ionic liquids (including isoparaffin-olefin alkylation reactions) are generally biphasic and occur at the interface in the liquid state. The volume of ionic liquid catalyst in the reactor may be generally in the range from about 1 to 70 vol %, and usually from about 4 to 50 vol %. Generally, vigorous stirring is used to ensure good contact between reactants and catalyst. The reaction temperature may be generally in the range from about −40° C. to +250° C., typically from about −20° C. to +100° C., and often from about +5° C. to +60° C. The reactor pressure may be in the range from atmospheric pressure to about 8000 kPa. Typically, the reactor pressure is sufficient to keep the reactants in the liquid phase.

Residence time of reactants in the reactor may generally be in the range from a few seconds to hours, and usually from about 0.5 min to 60 min. In the case of ionic liquid catalyzed isoparaffin-olefin alkylation, the reactants may be introduced in an isoparaffin:olefin molar ratio generally in the range from about 1 to 100, more typically from about 2 to 50, and often from about 2 to 20. Heat generated by the reaction may be dissipated using various means well known to the skilled artisan.

The following examples are illustrative of the present invention, but are not intended to limit the invention in any way beyond what is contained in the claims which follow.

EXAMPLES

Example 1

Ionic Liquid Catalyst Comprising Anhydrous Metal Halide

Various ionic liquid catalysts made of metal halides such as $AlCl_3$, $AlBr_3$, $GaCl_3$, $GaBr_3$, $InCl_3$, and InBr3 could be used for the catalytic processes. N-butylpyridinium heptachlorodialuminate ($C_5H_5NC_4H_9Al_2Cl_7$) ionic liquid catalyst is an example used in our process. The catalyst has the following composition.

| | |
|---|---|
| Wt % Al | 12.4 |
| Wt % Cl | 56.5 |
| Wt % C | 24.6 |
| Wt % H | 3.2 |
| Wt % N | 3.3 |

Example 2

Startup of a $C_3$ and $C_4$ Olefin/Isobutane Alkylation Process

Evaluation of $C_3$ and $C_4$ olefins alkylation with isobutane was performed in a continuously stirred tank reactor of an ionic liquid catalyzed alkylation system. In addition to the reactor, the system further included a gravity separator, a catalyst regeneration section, and a distillation section.

Before the start of the run, the system was dried with dry $N_2$ purge gas to remove any trapped air and free water. A first dryer vessel and a second dryer vessel, each charged with 13X molecular sieve dryerant, were used to dry the isobutane feed (both fresh and recycle isobutane), and the olefin feed, respectively. A third dryer vessel charged with 3A molecular sieve was used to dry t-butyl chloride catalyst promoter. The molecular sieve dryerants in each of the dryer vessels were previously activated with 5 v/v/min dry $N_2$ gas flow at 600° F. for 12 hours.

Then the dry isobutane feed was introduced to the reactor section, the distillation section, and the regeneration section; and the isobutane feed was re-circulated through the system via the isobutane dryer vessel. The moisture levels in various parts of the system were monitored with on-line moisture analyzers. By re-circulating the dried isobutane feed through the system via the dryer, the residual water content of the isobutane feed was gradually lowered to less than 10 ppm. Once the recycle isobutane feed was thoroughly dried in this manner, the isobutane feed was recycled directly to the reactor.

Then a small amount of butyl chloride promoter was introduced into the reactor by a first inlet port, followed by introduction of the ionic liquid catalyst (Example 1) to the reactor via a second inlet port to a catalyst volume of 6 vol %, while vigorously stirring the reactor. The butyl chloride was added in an amount corresponding to an olefin to organic chloride molar ratio of 20:1 upon the introduction of the olefin feed (described hereinbelow). The reactor outlet pressure was maintained at 200 psig and the reactor temperature was maintained at 70° F. using external cooling. The reactor effluent was separated with a gravity separator with a coalescing pad into a hydrocarbon phase and an ionic liquid catalyst phase. The catalyst phase was recycled back to the reactor directly.

Then the dried olefin feed was introduced into the reactor, with vigorous stirring, to provide an isobutane to olefin molar ratio of 8:1. The average residence time in the reactor (combined volume of feeds and catalyst) was about 4 minutes.

As alkylate gasoline was synthesized, the distillation column temperatures were adjusted to produce pure streams of propane product, n-butane product, and $C_5^+$ alkylate gasoline product, as well as isobutane recycle feed. The isobutane recycle stream was returned to the reactor, and fresh make-up isobutane was fed to the reactor as isobutane was consumed by the alkylation process.

While the distillation section of the system was operating and producing product, the catalyst regeneration system was prepared for regeneration of the ionic liquid catalyst. A fraction, 5-50% of the catalyst was diverted to the regeneration section and the rest of the catalyst phase was recycled back to the reactor directly. The regeneration reactor temperature was raised gradually to maintain the overall process performance.

The catalyst was sampled daily to determine the conjunct polymer concentration in the ionic liquid catalyst phase, and the conjunct polymer level in the catalyst was maintained at 5-15 wt % by adjusting the severity of catalyst regeneration and the amount of catalyst draining. A method for the quantification of conjunct polymer in ionic liquid catalyst is described, e.g., in Example 3 of U.S. Pat. No. 7,674,739 to Elomari et al., the disclosure of which is incorporated by reference herein in its entirety.

Shut down of ionic liquid catalyst based process runs may be needed on occasion to accommodate equipment service and maintenance or for various other reasons. As an example, ionic liquid catalyzed isoparaffin-olefin alkylation processes may be safely shut down using the procedure of Example 3.

Example 3

Shutdown and Re-Start Procedure for Ionic Liquid Catalyzed $C_3$ and $C_4$ Olefin/Isobutane Alkylation First, the olefin feed injection was stopped. Then the circulation of the ionic liquid catalyst and butyl chloride promoter was stopped. Thereafter, isobutane flow was continued for several hours to flush any reactive olefins from the reactor section, after which time the isobutane flow was turned off. The heaters for the distillation columns were also turned off.

Once the process has been safely "parked" according to the above procedure, any required service or maintenance of the system may be performed. When the service or maintenance has been completed, the process may be put back on stream, e.g., using the startup procedure of Example 2. If the shutdown is limited to only a portion of the system, a simpler startup procedure may be used and some of the steps described in Example 2 may be omitted, as appropriate.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A method for starting up a chloroaluminate ionic liquid catalyzed alkylation system, the method comprising:
   a) purging air and free water from at least a portion of the system;
   b) introducing at least one reactant into the at least a portion of the system;
   c) via at least one feed dryer unit, re-circulating the at least one reactant through the at least a portion of the system until the at least one reactant exiting the at least a portion of the system has a water content at or below a threshold value of 10 ppm; and
   d) after step c), introducing a chloroaluminate ionic liquid catalyst into a reactor of the system.

2. The method of claim 1, wherein:
   the system comprises a separation unit in fluid communication with the reactor, a distillation unit in fluid communication with the separation unit, and a catalyst regeneration unit in fluid communication with the separation unit and with the reactor, and
   the at least a portion of the system is selected from the group consisting of the reactor, the separation unit, the distillation unit, the catalyst regeneration unit, and combinations thereof.

3. The method of claim 1, wherein step a) comprises purging the at least a portion of the system with dry nitrogen gas or dry isobutane.

4. The method of claim 1, wherein:
   step a) comprises purging the at least a portion of the system with dry nitrogen gas and further comprises purging the at least a portion of the system with dry isobutane.

5. The method of claim 1, further comprising:
   e) after initiation of step b) and prior to initiation of step d), introducing a catalyst promoter into the reactor.

6. The method of claim 5, wherein the catalyst promoter comprises anhydrous HCl or an alkyl halide.

7. The method of claim 1, wherein:
   the at least one reactant comprises a first reactant and a second reactant,
   the at least one feed dryer unit comprises a first feed dryer unit and a second feed dryer unit, and the method further comprises:
   f) drying the first reactant via the first feed dryer unit; and
   g) drying the second reactant via the second feed dryer unit, wherein the first reactant comprises a $C_4$ to $C_{10}$ isoparaffin and the second reactant comprises a $C_2$ to $C_{10}$ olefin.

8. The method of claim 7, wherein:
   step b) comprises introducing the first reactant and the second reactant into the reactor,
   the first reactant is introduced into the reactor before step d), and
   the second reactant is introduced into the reactor after step d).

9. The method of claim 2, wherein:
   the at least one reactant comprises a $C_4$ to $C_{10}$ isoparaffin, and the method further comprises:
   h) after the water content has attained the threshold value according to step c), recycling the $C_4$ to $C_{10}$ isoparaffin from the distillation unit directly to the reactor.

10. The method of claim 7, further comprising:
    i) contacting the first and second reactants with the ionic liquid catalyst under alkylating conditions to form an alkylate product;
    j) separating the ionic liquid catalyst from a hydrocarbon phase containing the alkylate product; and
    k) feeding at least a portion of the hydrocarbon phase to the distillation unit.

11. The method of claim 10, further comprising:
    l) adjusting distillation conditions of the distillation unit to provide the alkylate product under steady state distillation conditions.

12. The method of claim 1, wherein:
    the system includes a catalyst regeneration unit for regenerating the ionic liquid catalyst, and the method further comprises:
    m) adjusting the catalyst regeneration unit to provide steady state catalytic activity of the reactor.

13. The method of claim 1, wherein the chloroaluminate ionic liquid catalyst comprises N-butylpyridinium heptachlorodialuminate.

14. A method for starting up a chloroaluminate ionic liquid catalyzed alkylation system, the method comprising:
    a) purging air and free water from the system, wherein the system comprises a reactor, a distillation unit in fluid communication with the reactor, and a catalyst regeneration unit in fluid communication with the reactor;
    b) introducing at least one reactant into the system;
    c) via at least one feed dryer unit, re-circulating the at least one reactant through the system until the at least one reactant exiting the system has a water content at or below a threshold value of 10 ppm;
    d) after the water content has attained the threshold value according to step c), introducing a catalyst promoter into the reactor; and
    e) after step d), introducing a chloroaluminate ionic liquid catalyst into the reactor.

15. The method of claim 14, further comprising:
    f) contacting the at least one reactant with the ionic liquid catalyst in the reactor to form at least one hydrocarbon product;
    g) separating the ionic liquid catalyst from a hydrocarbon phase containing the at least one hydrocarbon product;

h) feeding at least a portion of the hydrocarbon phase to the distillation unit;

i) adjusting distillation conditions of the distillation unit to provide the at least one hydrocarbon product under steady state distillation conditions; and j) adjusting the catalyst regeneration unit to provide steady state catalytic activity of the reactor.

16. A method for starting up a chloroaluminate ionic liquid catalyzed alkylation system, the method comprising:

a) purging air and free water from the system, wherein the system comprises a reactor, a distillation unit in fluid communication with the reactor, and a catalyst regeneration unit in fluid communication with the reactor;

b) recycling a dried feed through the system, via a feed dryer unit, until the residual water content of the feed is at or below a threshold value of 10 ppm;

c) after the water content has attained the threshold value according to step b), introducing at least one reactant into the reactor;

d) after initiation of step c), introducing a catalyst promoter into the reactor;

e) after initiation of step d), introducing a chloroaluminate ionic liquid catalyst into the reactor;

f) contacting the at least one reactant with the ionic liquid catalyst in the reactor to form at least one hydrocarbon product;

g) separating the ionic liquid catalyst from a hydrocarbon phase containing the at least one hydrocarbon product;

h) feeding at least a portion of the hydrocarbon phase to the distillation unit;

i) adjusting distillation conditions of the distillation unit to provide the at least one hydrocarbon product under steady state distillation conditions; and j) adjusting the catalyst regeneration unit to provide steady state catalytic activity of the reactor.

17. The method of claim 16, wherein:

the dried feed comprises isobutane, the catalyst promoter comprises t-butyl chloride or n-butyl chloride, and the at least one hydrocarbon product comprises a $C_5$ to $C_{16}$ alkylate.

* * * * *